US00PP17975P3

(12) United States Plant Patent
Olesen

(10) Patent No.: US PP17,975 P3
(45) Date of Patent: Sep. 4, 2007

(54) **BOTANICAL CLASSIFICATION *ROSA* HYBRID VARIETY DENOMINATION 'POULPAR036'**

(50) Latin Name: ***Rosa* hybrid**
Varietal Denomination: Poulpar036

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 11/337,255

(22) Filed: Jan. 19, 2006

(65) Prior Publication Data

US 2007/0169234 P1 Jul. 19, 2007

(51) Int. Cl.
*A01H 5/00* (2006.01)

(52) U.S. Cl. ..... Plt./117

(58) Field of Classification Search ..... Plt./117
See application file for complete search history.

*Primary Examiner*—Anne Marie Grunberg
*Assistant Examiner*—Annette H Para

(57) ABSTRACT

A new miniature rose plant which has abundant, white flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical classification: *Rosa* hybrid.
Variety denomination: 'Poulpar036'.

SUMMARY OF THE INVENTION

The present invention constitutes a new and distinct variety of miniature rose plant which originated from a controlled crossing between the female parent 'Korklevia', described and illustrated in U.S. Plant Pat. No. 11,232 and the male pollen parent, an unnamed seedling. The two parents were crossed, and the resulting seeds were planted in a controlled environment. The new variety is named 'Poulpar036'.

The new rose may be distinguished from its seed parent 'Korklevia' by the following combination of characteristics:

1. Petal count for 'Poulpar036' is 85. 'KORklevia' has 25 to 30 petals.
2. Flower diameter of 'Poulpar036' is 55 mm, while 'Korklevia' is 38 to 44 mm.

The new variety may be distinguished from its pollen parent by the following combination of characteristics:

1. 'Poulpar036' has a flower diameter of 55 mm while the pollen parent has a smaller diameter of 25 to 30 mm.
2. 'Poulpar036' has near white colored flowers while the pollen parent has light pink flowers.

The objective of the hybridization of this rose variety for commercial culture was to create a new and distinct variety with unique qualities, such as:

1. Uniform and abundant near white flowers;
2. Vigorous and compact growth;
3. Year-round flowering under glasshouse conditions;
4. Suitability for production from softwood cuttings in 10 to 15 cm pots;
5. Durable flowers and foliage which make a variety suitable for distribution in the floral industry.

This combination of qualities is not present in previously available commercial cultivars of this type, known to the inventor, and distinguish 'Poulpar036' from all other varieties of which we are aware.

As part of the rose development program, Mogens N. Olesen germinated the seeds from the aforementioned hybridization and conducted evaluations on the resulting seedlings in a controlled environment in Fredensborg, Denmark.

'Poulpar036' was selected by the inventor as a single plant from the progeny of the hybridization in June 2001.

Asexual reproduction of 'Poulpar036' by cuttings and traditional budding was first done by Mogens N. Olesen in the nursery in Fredensborg, Denmark in April 2002. This initial and other subsequent propagations conducted in controlled environments have demonstrated that the characteristics of 'Poulpar036' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpar036'. Specifically illustrated in the drawing:

FIG. 1.1; Flower buds at various stages of opening, showing pedicel and receptacle characteristics;

FIG. 1.2; Open flower and petals detached;

FIG. 1.3; Above view of reproductive parts and sepals;

FIG. 1.4; Mature leaves, upper surface;

FIG. 1.5; Bare stem;

FIG. 1.6; Leaf undersurface.

DETAILED DESCRIPTION OF THE VARIETY

The following is a description of 'Poulpar036', as observed in its growth in glasshouses in Odense, Denmark. Observed plants are 4 months of age and were cultivated in 10.5 cm pots. Color references are made using The Royal Horticultural Society (London, England) Colour Chart, 2001, except where common terms of color are used.

For a comparison, several physical characteristics of the rose variety 'Poulra015', a rose variety from the same inventor, described and illustrated in U.S. Plant Pat. No. 14,309 and issued on Nov. 18, 2003, are compared to 'Poulpar036' in Chart 1.

CHART 1

| | 'Poulpar036' | 'Poulra015' |
|---|---|---|
| Petalage | 85 | 13 to 15 |
| Upon opening, inner petal, upper surface. | Yellow Group 4D. | Yellow Group 11D. |
| Bud color as sepals unfold, upper surface. | Yellow-White Group 158B with intonations of Yellow-Green Group 145A and Greyed-Purple Group 184C. | Yellow-White Group 158C. |

FLOWER AND FLOWER BUD

Blooming habit: Continuous.

Flower bud:

*Size.*—Upon opening, 18 mm in length from base of receptacle to end of bud. 13 mm in diameter on average.

*Bud form.*—Pointed ovoid, somewhat broadened.

*Bud color.*—As sepals unfold, Yellow-White Group 158B with light intonations of Yellow-Green Group 145A and Greyed-Purple Group 184C.

*Sepals.*—Upper Surface: Color: As flowers begin to develop, sepals are Yellow-Green Group 147A to 147B with intonations of Greyed-Red Group 178A at apex. As flowers continue to mature sepals become Yellow-Green Group 147A. Texture: Varies from strongly pubescent to absence of pubescence. Lower Surface: Color: As flowers begin to develop, sepals are Yellow-Green Group 147B. As flowers mature, sepals become Yellow-Green Group 148B. Texture: Smooth. Few stipitate glands and sparse pubescence. Shape and Size: As flowers begin to develop, sepals are cirrhose, 28 mm in length, by 7 mm wide. As the flowers further develop, sepals broaden becoming 55 to 60 mm in length by 20 to 30 mm wide. General shape of the sepals becomes elliptical. Margins: Margins have strong foliaceous appendages.

*Receptacle.*—Surface Texture: Smooth. Shape: Funnel shaped. Size: 5 to 10 mm (h)×10 mm (w). Color: Yellow-Green Group 144A.

*Pedicel.*—Surface: Smooth to slightly rough with stipitate glands. Length: 20 to 60 mm. Diameter: 3 mm on average. Color: Yellow-Green Group 144A. Strength: Strong.

*Borne.*—Normally singularly.

Flower bloom:

*Fragrance.*—Medium floral scent.

*Duration.*—As a potted plant, flowers last up to 18 days. Petals do not fall cleanly away from plant after flowers have matured.

*Size.*—Flower diameter is normally 55 mm. Average flower depth is 25 mm when open.

*Form.*—General shape is calathiform rosette with densely packed petals. Shape of flower when viewed from the side: Upon opening, Upper part: Flat. Lower part: Flat. Open flower, Upper part: Flattened convex. Lower part: Concave.

*Petalage.*—Normally 85 petals, 15 of which are petaloids.

Color:

*Upon opening, petals.*—Outermost petals: Upper Surface: Yellow-Green Group 145C. Outermost guard petals have strong intonations of Yellow-Green Group 145B at their margins. Lower Surface: Yellow-Green Group 145D to Yellow-White Group 158B. Outermost guard petals have strong intonations of Yellow-Green Group 145C at their margins. Occasionally, vertical streaks the color of Greyed-Purple 184C occur in the outermost petals. Innermost petals: Upper Surface: Yellow Group 4D. Lower Surface: Yellow Group 4D.

*Upon opening, basal petal spots.*—Upper Surface: Yellow Group 4B at point of attachment. Lower Surface: None.

*After opening, petals.*—Outermost petals: Upper Surface: Yellow-Green Group 145C. Guard petals have intonations of Yellow-Green Group 145B from the middle to marginal zone. Lower Surface: Yellow-Green Group 145D to Yellow-White Group 158B. Guard petals have intonations of Yellow-Green Group 145C from the middle to marginal zone. Occasionally, vertical streaks the color of Greyed-Purple 184C appear in the outermost petals. Innermost petals: Upper Surface: Yellow Group 4D. Lower Surface: Yellow Group 4D.

*After opening, basal petal spots.*—Upper Surface: Yellow Group 4B at point of attachment. Lower Surface: None.

General tonality: On open flower Yellow Group 8D with the outer whorl of guard petals having intonations of Yellow-Green Group 145B. No change in the general tonality at the end of the 15$^{th}$ day. Afterwards, general tonality becomes Yellow-Green Group 145D.

Petals:

*Petal reflex.*—Double to quadruple reflexing.

*Petal margin.*—Entire. Very strong undulations of margin observed in outermost petal layer. Moving towards the flower center petals have medium undulations of margin.

*Shape.*—Broad elliptical. Base: Obtuse. Apex: Rounded.

*Size.*—22 to 30 mm (l)×18 to 40 mm (w).

*Thickness.*—Above average.

*Texture.*—Majority of petals are smooth. Guard petals are somewhat rough.

Petaloids:

*Quantity.*—15 on average.

*Size.*—15 mm (l)×12 mm (w).

*Shape.*—Elliptical to irregular in shape.

*Color.*—Upper surface: Yellow Group 4D. Lower Surface: Yellow Group 4D. Margins: Undulating strongly.

Reproductive organs:

*Pollen.*—None observed.

*Anthers.*—Size: 2 mm long. Color: Yellow-Orange Group 22A to 21A. Quantity: 55 to 65.

*Filaments.*—Color: Yellow Group 5A. Length: On average, 5 mm.

*Pistils.*—Length: 5 to 8 mm. Quantity: 60 to 70.

*Stigmas.*—Superior in location relative to the length of the filaments and the height of the anthers. Color: Greyed-Yellow Group 162D.

*Styles.*—Color: White Group 155A with Red-Purple Group 58B toward the stigma.

*Seed formation.*—Not observed.

PLANT

Plant growth: Vigorous, compact, upright and moderately bushy. When grown as an 10.5 cm pot plant on its own roots, the average height of the plant itself is up to 30 cm. Average spread is 25 cm.

Stems:

*Color.*—Mature and juvenile stems are Yellow-Green Group 144B.

*Internodal distance.*—20 mm.

*Length of stems.*—Normally 20 cm from the base of the plant to the flowering portion.

*Diameter.*—2.75 mm on average.

*Surface texture.*—Mature and juvenile wood is smooth.

Prickles:

*Incidence.*—8 to 10 prickles per 10 cm of stem.

*Size.*—4 to 5 mm.

*Color.*—Juvenile and mature prickles are Greyed-Red Group 181C.

*Shape.*—Upper side: Flat. Lower side: Flat.

Plant foliage: Normally 5 leaflets at mid stem.

*Compound leaf size.*—On average, 80 mm (l)×60 mm (w).

*Quantity.*—5 leaves per 10 cm of stem.

*Color of juvenile foliage.*—Upper Surface: Green Group 138A. Lower Surface: Green Group 138B with light overlay of Greyed-Purple Group 182A.

*Color of mature foliage.*—Upper Leaf Surface: Yellow-Green Group 147A. Lower Leaf Surface: Yellow-Green Group 147B.

Plant leaves and leaflets:

*Stipules.*—Size: 10 mm. Shape: Linear, slightly broad based with outward extending apecies. Margins: Finely serrated with few stipitate glands. Color: Yellow-Green Group 146B.

*Petiole.*—Length: 15 to 20 mm. Diameter: 1 mm. Petiole Color: Upper surface is Yellow-Green Group 144A with intonations of Greyed-Purple Group 183A. The lower surface is Yellow-Green Group 145A. Observations: Few stipitate glands and 1 small prickle 2 mm in length observed.

*Rachis.*—Size: 15 to 20 mm in length. Rachis Color: Upper surface is Yellow-Green Group 144A with light anthocyanic intonations of Greyed-Purple Group 183A. The lower surface is Yellow-Green Group 145A. Underside: Few stipitate glands present. Few long prickles observed on the underside which are 2 mm length.

*Leaflet.*—Size: On average, 42 mm in (l)×24 mm (w). Margin: Doubly serrated. Shape: Generally ovate. The apex is acuminate. Base shape is obtuse. Texture: Smooth. Thickness: Average to thin. Arrangement: Odd pinnate. Venation: Reticulate. Leaf Gloss: Matte finish.

Disease resistance: Average resistance to downy and powdery mildew, black spot, and *Botrytis* under normal growing conditions in Odense, Denmark.

What is claimed is:

1. A new and distinct variety of rose plant of the miniature class named 'Poulpar036', substantially as illustrated and described herein, due to its abundant, white flowers, vigorous growth, compact habit, suitability for production from softwood cuttings in pots, and durable flowers and foliage that make the variety suitable for distribution in the floral industry.

* * * * *

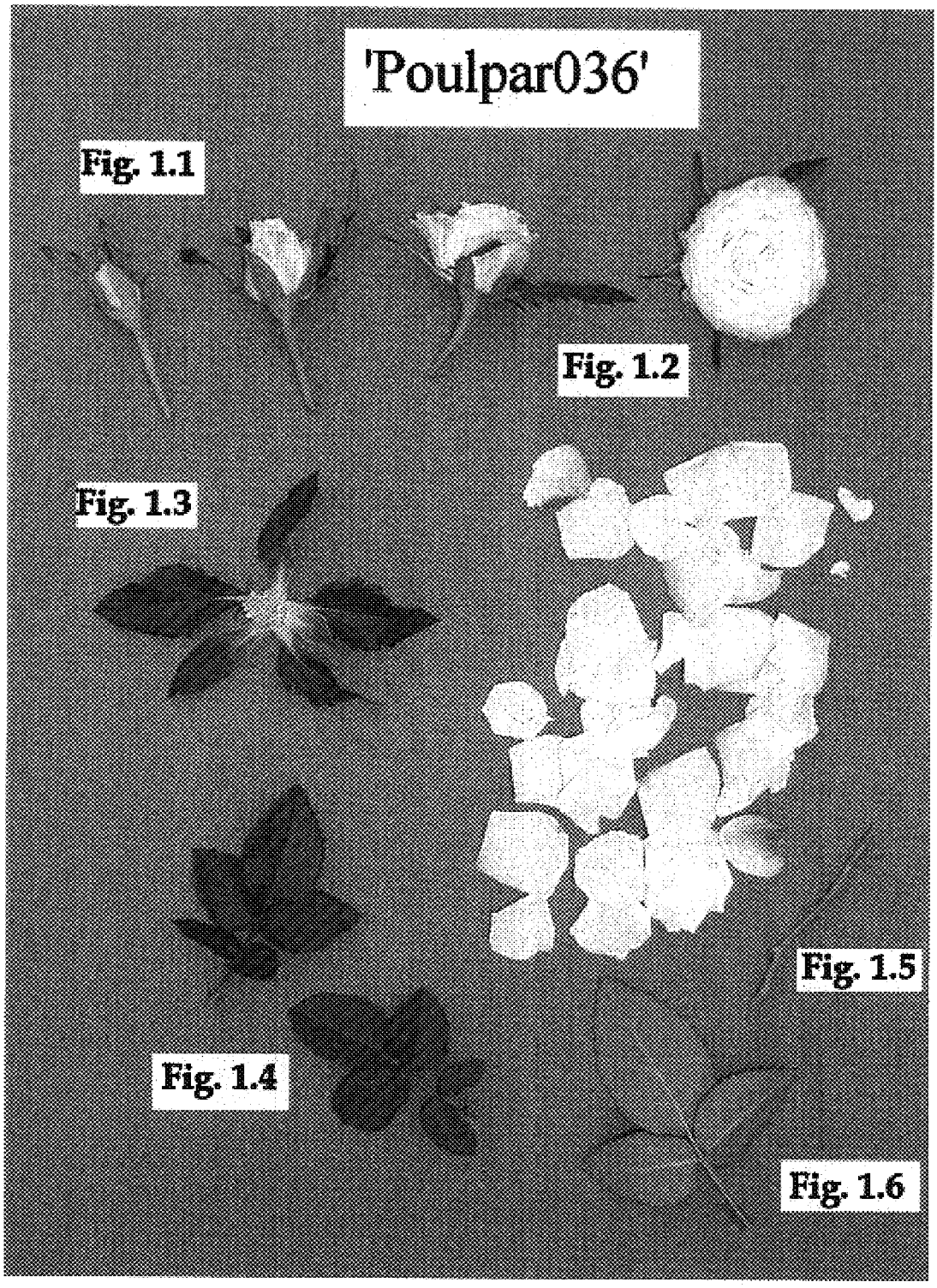
'Poulpar036'
Fig. 1.1
Fig. 1.2
Fig. 1.3
Fig. 1.4
Fig. 1.5
Fig. 1.6